United States Patent
Kitamura

(10) Patent No.: US 7,902,405 B2
(45) Date of Patent: Mar. 8, 2011

(54) PROCESS FOR PRODUCTION OF 2,6-DIMETHYL-1-NAPHTHALDEHYDE

(75) Inventor: Mitsuharu Kitamura, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 12/446,800

(22) PCT Filed: Oct. 19, 2007

(86) PCT No.: PCT/JP2007/070474
§ 371 (c)(1),
(2), (4) Date: Apr. 23, 2009

(87) PCT Pub. No.: WO2008/050691
PCT Pub. Date: May 2, 2008

(65) Prior Publication Data
US 2010/0004488 A1    Jan. 7, 2010

(30) Foreign Application Priority Data
Oct. 26, 2006    (JP) ................. 2006-291554

(51) Int. Cl.
*C07C 45/49* (2006.01)
(52) U.S. Cl. ........................................ 568/428
(58) Field of Classification Search ............. 568/428
See application file for complete search history.

(56) References Cited

U.S. PATENT DOCUMENTS

| | | | | |
|---|---|---|---|---|
| 2,485,237 A | * | 10/1949 | Gresham et al. | 568/428 |
| 4,460,794 A | | 7/1984 | Fujiyama et al. | |
| 5,068,450 A | * | 11/1991 | Crochemore et al. | 568/435 |
| 6,881,866 B2 | * | 4/2005 | Kato et al. | 568/428 |
| 2004/0092776 A1 | | 5/2004 | Kato et al. | |

FOREIGN PATENT DOCUMENTS

| | | |
|---|---|---|
| EP | 1 380 560 | 1/2004 |
| JP | 50-117737 | 9/1975 |
| JP | 63-002943 | 1/1988 |
| JP | 08-268990 | 10/1996 |
| JP | 2004-43362 | 2/2004 |
| JP | 2007-262059 | 10/2007 |

OTHER PUBLICATIONS

L.E. Hinkel et al., J. Chem. Soc., 1936, pp. 339-346.
F.M. Aslam et al., J. Chem. Soc., Perkin I, 1972, pp. 892-894.

* cited by examiner

*Primary Examiner* — Sikarl A Witherspoon
(74) *Attorney, Agent, or Firm* — Greenblum & Bernstein, P.L.C.

(57) ABSTRACT

2,6-Dimethyl-1-naphthaldehyde having a ratio of the amount of 3,7-dimethyl-1-naphthaldehyde to the total amount of 2,6-dimethyl-1-naphthaldehyde and 3,7-dimethyl-1-naphthaldehyde of 30 mol % or less is particularly useful as optical functional materials, etc. The present invention provides a process for producing such 2,6-dimethyl-1-naphthaldehyde in an industrially advantageous manner. Specifically, in the process for producing 2,6-dimethyl-1-naphthaldehyde through formylation of 2,6-dimethylnaphthalene with carbon monoxide, formylation is performed in the presence of hydrogen fluoride in an amount of 5 to 100 times by mole and boron trifluoride in an amount of 0.5 to 3.5 times by mole, with respect to 2,6-dimethylnaphthalene, and at a reaction temperature of 35 to 70° C.

3 Claims, No Drawings

PROCESS FOR PRODUCTION OF 2,6-DIMETHYL-1-NAPHTHALDEHYDE

TECHNICAL FIELD

The present invention relates to a process for producing 2,6-dimethyl-1-naphthaldehyde, which is useful for industrial chemical materials and starting materials for pharmaceuticals, pesticides, optical functional materials, electronic functional materials, etc.

BACKGROUND ART

Hitherto, naphthaldehydes have been generally synthesized through known processes. Examples of such processes include a process for producing 7-methyl-1-naphthaldehyde, including reacting 2,7-dimethylnaphthalene with a halogenating agent, to form a monohalogenated species, and oxidizing the produced 7-methyl-2-halogenomethylnaphthalene (see Patent Document 1); a process for producing aromatic aldehydes, including reacting an aromatic halomethyl compound with nitric acid in the presence of a surfactant (see Patent Document 2); a process for producing dimethylnaphthaldehyde, including adding aluminum chloride to a mixture containing hydrogen chloride, zinc cyanide, and dimethylnaphthalene (see Non-Patent Document 1); and a production process including converting alkylnaphthalene to alkylnaphthaldehyde in the presence of hydrogen cyanide and aluminum chloride (see Non-Patent Document 2). Another known process for producing dialkylbenzaldehyde from dialkylbenzene includes reacting dialkylbenzene with carbon monoxide in the presence of a catalyst formed from hydrogen fluoride and boron trifluoride (see Patent Document 3).

Patent Document 1: Japanese Patent Application Laid-Open (kokai) No. 08-268990
Patent Document 2: Japanese Patent Application Laid-Open (kokai) No. 50-117737
Patent Document 3: U.S. Pat. No. 4,460,794
Non-Patent Document 1: F. M. Aslam and P. H. Gore, J. Chem. Soc., Perkin Trans. I, 1972, p. 892 and 893
Non-Patent Document 2: L. E. Hinkel, E. E. Ayling, and J. H. Beynon, J. Chem. Soc., 1936, p. 339 and 342

DISCLOSURE OF THE INVENTION

Problems to be Solved by the Invention

In the process disclosed in Patent Document 1, a halogenating agent such as N-bromosuccinimide is preferably used. However, such an expensive agent as N-bromosuccinimide is disadvantageous in cost. In addition, use of an amine in an oxidation step imposes a heavy load on the environment, and the process is not suited for large-scale production. Although the processes disclosed in Patent Documents 1 and 2 essentially include transformation of a methyl group to a formyl group, no process has been hitherto disclosed in which a formyl group is introduced to a site on the aromatic ring where no methyl group is bonded, while maintaining a methyl group on the aromatic ring.

The processes disclosed in Non-Patent Documents 1 and 2 employ a cyan compound, which imposes a heavy load on the environment. Therefore, these processes are difficult to actually carry out on an industrial scale, and attain low reaction activity and productivity, which are problematic.

The process disclosed in Patent Document 3 is a promising candidate for an industrial production process, since the employed catalyst can be readily recycled. Thus, the present inventors previously attempted to introduce a formyl group to 2,6-dimethylnaphthalene serving as a starting material under the conditions disclosed in Patent Document 3. As a result, in addition to 2,6-dimethyl-1-naphthaldehyde employed as an optical functional material, an almost equiamount of 3,7-dimethyl-1-naphthaldehyde was produced as a by-product. Since these two isomers have nearly equal boiling points, the isomers are difficult to separate from each other even when the mixture is subjected to distillation. Rectification with a large number of stages is a possible approach for separating the isomers. However, this approach is not economically advantageous unless a by-product 3,7-DMNAL is effectively utilized. When 2,6-dimethyl-1-naphthaldehyde is employed as an optical functional material, the 3,7-dimethyl-1-naphthaldehyde content thereof is lowered to 30 mol % or less. Therefore, there is demand for a reliable process for producing 2,6-dimethyl-1-naphthaldehyde at high selectivity.

Means for Solving the Problems

In view of the foregoing, the present inventors have carried out extensive studies on a reliable, high-selectivity process for producing 2,6-dimethyl-1-naphthaldehyde from 2,6-dimethylnaphthalene and carbon monoxide in the presence of a catalyst formed from hydrogen fluoride and boron trifluoride, and have found that the ratio of the amount of formed 3,7-dimethyl-1-naphthaldehyde to the total amount of formed 2,6-dimethyl-1-naphthaldehyde and 3,7-dimethyl-1-naphthaldehyde is determined at the time of formylation and does not vary through distillation for purification or other processes. The inventors have also found that the ratio can be constantly suppressed to 30 mol % or less by appropriate selection of formylation conditions. The present invention has been accomplished on the basis of these findings.

Accordingly, the present invention provides a process for producing 2,6-dimethyl-1-naphthaldehyde through formylation of 2,6-dimethylnaphthalene with carbon monoxide, characterized in that formylation is performed in the presence of hydrogen fluoride in an amount of 5 to 100 times by mole and boron trifluoride in an amount of 0.5 to 3.5 times by mole, with respect to 2,6-dimethylnaphthalene, and at a reaction temperature of 35 to 70° C.

EFFECTS OF THE INVENTION

According to the process of the present invention, 2,6-dimethyl-1-naphthaldehyde, which is useful for industrial chemical materials and starting materials for pharmaceuticals, pesticides, optical functional materials, and electronic functional materials, can be produced in an industrially advantageous manner at a ratio of the amount of 3,7-dimethyl-1-naphthaldehyde to the total amount of 2,6-dimethyl-1-naphthaldehyde and 3,7-dimethyl-1-naphthaldehyde of 30 mol % or less.

BEST MODES FOR CARRYING OUT THE INVENTION

In the present invention, 2,6-dimethylnaphthalene (hereinafter this is referred to as 2,6-DMN, and an isomer 2,7-dimethylnaphthalene is referred to as 2,7-DMN) serving as a starting material is a known white compound having a melting point of 111° C. and a boiling point of 262° C. (under ambient pressure). No particular limitation is imposed on the method for producing 2,6-DMN, and a known production method may be employed. In one method for producing 2,6-DMN, coal tar, a petroleum fraction, or the like is appropriately diluted with toluene or a similar solvent, followed by sufficient cooling, to thereby precipitate 2,6-DMN and 2,7-DMN. The two separated species are dissolved in a solvent such as m-xylene, and the solution is caused to pass through an adsorbent, to thereby selectively obtain high-purity 2,6-DMN (see, for example, Japanese Kohyo Patent Publication No. 2001-527054). In another method, naphthalene or methylnaphthalene is transalkylated and isomerized in the presence of a zeolite catalyst and by employment of polymethylbenzene, and 2,6-DMN is separated from the reaction mixture through, for example, distillation (see, for example, Japanese Patent Application Laid-Open (kokai) No. 6-040958). In still another method, 1,5-dimethylnaphthalene produced from o-xylene and butadiene is isomerized in the presence of a catalyst such as hydrogen fluoride, and the isomerized product is mixed with aliphatic or alicyclic saturated hydrocarbon, followed by crystallization, to thereby separate 2,6-DMN (see, for example, Japanese Patent Application Laid-Open (kokai) No. 9-291045).

The method of the present invention of formylating 2,6-DMN with carbon monoxide is carried out in the presence of a catalyst formed from hydrogen fluoride (hereinafter referred to as HF) and boron trifluoride (hereinafter referred to as $BF_3$) (hereinafter the catalyst may be referred to as a $HF.BF_3$ catalyst). Since HF and $BF_3$ serving as a catalyst component have high volatility, these components can be recovered after reaction and recycled in the present invention. Thus, waste treatment of the formylation catalyst is not necessary, making the method economically advantageous and reducing an environmental load.

Carbon monoxide may contain an inert gas such as nitrogen or methane. The partial pressure of carbon monoxide is preferably 0.5 to 5 MPa, more preferably 1 to 3 MPa. Such a limitation in range of partial pressure is preferred, since formylation proceeds sufficiently, and a drop in production yield, which would otherwise be caused by side reactions such as isomerization and polymerization, can be suppressed to a low level.

HF is preferably anhydrous. More specifically, the water content of HF is preferably 0.1% or less, more preferably 0.02% or less. HF is used in an amount by mole of 5 to 100 times that of 2,6-DMN, preferably 5 to 50 times, more preferably 8 to 50 times, still more preferably 10 to 50 times, particularly preferably 10 to 30 times. When the amount by mole of HF is less than 5 times that of 2,6-DMN, percent selectivity of 2,6-dimethyl-1-naphthaldehyde decreases, whereas when the amount is in excess of 100 times, an effect commensurate with the amount of increase cannot be attained, which is economically disadvantageous.

$BF_3$ is used in an amount by mole of 0.5 to 3.5 times that of 2,6-DMN, preferably 0.7 to 3 times, more preferably 0.8 to 2 times, still more preferably 0.9 to 1.2 times. When the amount by mole of $BF_3$ is less than 0.5 times that of 2,6-DMN, progress of formylation is retarded, and percent selectivity of 2,6-dimethyl-1-naphthaldehyde decreases, whereas when the amount is in excess of 3.5 times, the partial pressure of carbon monoxide in the gas phase decreases, resulting in a decrease in production yield, which is not preferred.

In order to suppress the ratio of the amount of 3,7-dimethyl-1-naphthaldehyde (hereinafter referred to as 3,7-DMNAL) to the total amount of 2,6-dimethyl-1-naphthaldehyde (hereinafter referred to as 2,6-DMNAL) and 3,7-DMNAL (hereinafter referred to as 3,7 ratio) to 30 mol % or less, the aforementioned amounts of HF and $BF_3$ with respect to 2,6-DMN, and the temperature at which formylation is performed are important factors.

Generally, formylation in the presence of a $HF.BF_3$ catalyst is performed at about −30° C. to about 20° C. However, according to the process of the present invention, formylation is performed at 35 to 70° C., preferably 40 to 60° C., more preferably 45 to 55° C. Such a temperature range cannot be conceived by the common sense of those skilled in the art. When the amounts of HF and $BF_3$ with respect to 2,6-DMN fall within the aforementioned range, and the reaction temperature is controlled to 35 to 70° C., 2,6-DMNAL can be produced at high yield, while the 3,7 ratio can be constantly suppressed to 30 mol % or less. When the reaction temperature is lower than 35° C., the 3,7 ratio decreases, but reaction yield lowers considerably. Furthermore, large amounts of high-boiling-point compounds are by-produced, making industrial-scale formylation difficult to carry out. When the reaction temperature is higher than 70° C., production of high-boiling-point compounds is promoted, lowering the yield.

No particular limitation is imposed on the reaction time, and the time is preferably 1 to 10 hours, more preferably 1 to 5 hours. Generally, when such reaction time is selected, sufficient percent conversion of 2,6-DMN can be attained. The end point of reaction is indicated by the point in time when absorption of carbon monoxide has stopped.

The formylation may be performed in the absence or presence of solvent. No particular limitation is imposed on the solvent, so long as the solvent can dissolve 2,6-DMN and is inert to 2,6-DMN, HF, and $BF_3$. Examples of the solvent include saturated aliphatic hydrocarbons such as hexane, heptane, and decane. When solvent is employed, the amount of solvent by mass is preferably 0.1 to 10 times that of 2,6-DMN, more preferably 0.5 to 3 times. Use of solvent further suppresses polymerization (side reaction), elevating the production yield. However, if a large amount of solvent is used, reaction efficiency in terms of volume decreases, and excess energy is required for separation of the product, impairing energy unit.

No particular limitation is imposed on the format of formylation of the present invention, so long as the gas phase and the liquid phase are sufficiently mixed by stirring. Any of the batch manner, semi-batch manner, continuous manner, etc. may be employed. Hereinafter, the specific modes of the batch manner, semi-batch manner, and continuous manner will be described. However, the formylation format is not particularly limited thereto.

In the batch manner, 2,6-DMN dissolved in a solvent, a predetermined amount of anhydrous HF, and a predetermined amount of $BF_3$ are fed to a reactor, for example, an autoclave equipped with an electromagnetic stirrer. Under stirring the contents, the liquid temperature is maintained at 35 to 70° C. The pressure of the reactor is elevated to, for example, 0.5 to 3 MPa by feeding carbon monoxide thereto. The pressure is maintained by feeding carbon monoxide thereto, and the contents are maintained at the temperature for one hour, whereby 2,6-DMNAL can be produced. Formation of 2,6-DMNAL can be confirmed by sampling a portion of the reaction product liquid, pouring the portion into ice-water, and analyzing the formed oil layer through gas chromatography.

In the semi-batch manner, a predetermined amount of anhydrous HF and a predetermined amount of $BF_3$ are fed to a reactor, for example, an autoclave equipped with an electromagnetic stirrer. Under stirring the contents, the liquid temperature is maintained at 35 to 70° C. The pressure of the reactor is elevated to, for example, 0.5 to 3 MPa by feeding carbon monoxide thereto. Thereafter, in accordance with need, carbon monoxide is fed to the reactor in order to maintain the pressure. 2,6-DMN dissolved in a solvent was fed to the reactor over one hour. The mixture is maintained under the conditions for 20 minutes, whereby 2,6-DMNAL can be produced. Formation of 2,6-DMNAL can be confirmed by sampling a portion of the reaction product liquid, pouring the portion into ice-water, and analyzing the formed oil layer through gas chromatography.

In a continuous manner, an aliquot of anhydrous HF and an aliquot of $BF_3$ are fed to a reactor, for example, an autoclave equipped with an electromagnetic stirrer. Under stirring the contents, the liquid temperature is maintained at 35 to 70° C. The pressure of the reactor is elevated to, for example, 0.5 to 3 MPa by feeding carbon monoxide thereto. Thereafter, in accordance with need, carbon monoxide is fed to the reactor in order to maintain the pressure. Then, 2,6-DMN dissolved in a solvent is continuously fed to the reactor. The remaining portions of anhydrous HF and $BF_3$ are continuously or intermittently fed to the reactor. The reaction mixture is remained in the reactor for 1 to 5 hours. Thereafter, the liquid reaction mixture is continuously discharged to ice-water. Through gas chromatographic analysis of the formed oil layer, formation of 2,6-DMNAL can be confirmed.

The thus-obtained liquid reaction mixture is an HF solution containing a complex formed from 2,6-DMNAL and a $HF.BF_3$ catalyst and a complex formed from 3,7-DMNAL and a $HF.BF_3$ catalyst. Through heating, the bond between each DMNAL and the $HF.BF_3$ catalyst is cleaved, whereby HF and $BF_3$ can be separated through evaporation, and recycled. The thermal decomposition of the complexes is performed at a maximum speed, so as to prevent heat damage, isomerization, etc. of the formed products. Therefore, the thermal decomposition of the complexes is preferably performed under reflux with a solvent such as a saturated aliphatic hydrocarbon (e.g., heptane) or an aromatic hydrocarbon (e.g., benzene), the solvent being inert to the $HF.BF_3$ catalyst.

2,6-DMNAL may be separated from the obtained liquid reaction mixture and purified through a routine purification technique for organic compounds; such as distillation or column chromatography.

EXAMPLES

The present invention will next be described in detail by way of examples, which should not be construed as limiting the invention thereto. Notably, the following gas chromatographic analysis conditions were employed.
[Gas Chromatographic Analysis Conditions]
Chromatograph: GC-17A (product of Shimadzu Corporation)
Column employed: HR-1, capillary column (diameter: 0.32 mm×length: 25 m, product of Shinwa Chemical Industries Ltd.)
Analysis conditions: inlet temperature of 310° C. and detector temperature of 310° C.
Column temperature: 100° C. to 320° C., with elevation at 5° C./min
Detector: Flame ionization detector (FID)

Example 1

To a 1,000-mL autoclave (made of SUS 316L) equipped with a thermostat and an electromagnetic stirrer, 2,6-DMN (product of Mitsubishi Gas Chemical Company, Inc.) (100.0 g, 0.64 mol), n-heptane (100.0 g), anhydrous HF (320.2 g, 16.0 mol; 25 times by mole to 2,6-DMN), and $BF_3$ (47.8 g, 0.70 mol; about 1.1 times by mole to 2,6-DMN) were added. The temperature of the liquid was maintained at 50° C. under stirring of the contents. The pressure in the autoclave was elevated to 2 MPa by feeding carbon monoxide thereto. The conditions (2 MPa and 50° C.) were maintained for one hour. Thereafter, the formed reaction mixture was recovered and poured into ice-water, followed by neutralization, to thereby form an oil layer. Through gas chromatographic analysis of the oil layer, percent conversion of 2,6-DMN, 2,6-DMNAL yield, and 3,7-DMNAL yield were found to be 75.6%, 45.5%, and 18.6% (2,6-DMNAL/3,7-DMNAL=71.0/29.0), respectively.

The thus-obtained liquid was rectified through a rectifying column (theoretical stage: 20), and a main fraction (38.7 g) containing 2,6-DMNAL (71.0 mass %) and 3,7-DMNAL (28.0 mass %) (2,6-DMNAL/3,7-DMNAL=71.7/28.3) was obtained (2,6-DMNAL yield 32.8%, purity 71.0%). Notably, the isomer ratio was not varied after distillation.

Example 2

The procedure of Example 1 was repeated, except that anhydrous HF (320.2 g, 16.0 mol) was changed to anhydrous HF g, 19.2 mol; 30 times by mole to 2,6-DMN). The obtained oil layer was analyzed through gas chromatography. As a result, the percent conversion of 2,6-DMN, 2,6-DMNAL yield, and 3,7-DMNAL yield were found to be 66.0%, 44.9%, and 8.3% (2,6-DMNAL/3,7-DMNAL=84.4/15.6).

Example 3

The procedure of Example 1 was repeated, except that anhydrous HF (320.2 g, 16.0 mol) was changed to anhydrous HF (384.3 g, 19.2 mol; 30 times by mole to 2,6-DMN) and the liquid temperature was maintained at 50° C. for 3 hours instead of at 50° C. for 1 hour. The obtained oil layer was analyzed through gas chromatography. As a result, the percent conversion of 2,6-DMN, 2,6-DMNAL yield, and 3,7-DMNAL yield were found to be 93.5%, 48.8%, and 7.1% (2,6-DMNAL/3,7-DMNAL=87.3/12.7).

Example 4

The procedure of Example 1 was repeated, except that the liquid temperature was maintained at 60° C. for 1 hour instead of at 50° C. for 1 hour. The obtained oil layer was analyzed through gas chromatography. As a result, the percent conversion of 2,6-DMN, 2,6-DMNAL yield, and 3,7-DMNAL yield were found to be 84.2%, 37.4%, and 6.1% (2,6-DMNAL/3,7-DMNAL=85.9/14.1).

Comparative Example 1

The procedure of Example 1 was repeated, except that anhydrous HF (320.2 g, 16.0 mol) was changed to anhydrous HF (42.3 g, 2.1 mol; about 3.3 times by mole to 2,6-DMN). The obtained oil layer was analyzed through gas chromatography. As a result, the percent conversion of 2,6-DMN, 2,6-DMNAL yield, and 3,7-DMNAL yield were found to be 80.9%, 12.1%, and 25.2% (2,6-DMNAL/3,7-DMNAL=32.4/67.6).

Thus, when the amount of HF was reduced to less than 5 times by mole with respect to that of 2,6-DMN, the 3,7-ratio considerably exceeded 30 mol %, and the 2,6-DMNAL yield decreased.

Comparative Example 2

The procedure of Example 1 was repeated, except that the liquid temperature was maintained at 25° C. for 3 hours instead of at 50° C. for 1 hour. The obtained oil layer was analyzed through gas chromatography. As a result, the percent conversion of 2,6-DMN, 2,6-DMNAL yield, and 3,7-DMNAL yield were found to be 77.0%, 30.6%, and 37.4% (2,6-DMNAL/3,7-DMNAL=45.0/55.0).

Thus, when the reaction temperature was adjusted to lower than 35° C., the 3,7-ratio considerably exceeded 30 mol %.

Comparative Example 3

The procedure of Example 1 was repeated, except that the liquid temperature was maintained at 75° C. for 1 hour instead of at 50° C. for 1 hour. The obtained oil layer was analyzed through gas chromatography. As a result, the percent conversion of 2,6-DMN, 2,6-DMNAL yield, and 3,7-DMNAL yield were found to be 90.2%, 10.3%, and 0.8% (2,6-DMNAL/3,7-DMNAL=93.1/6.9).

Thus, when the reaction temperature was adjusted to exceed 70° C., large amounts of high-boiling-point compounds were by-produced, to thereby considerably reduce the 2,6-DMNAL yield.

Comparative Example 4

The procedure of Example 1 was repeated, except that $BF_3$ (47.8 g, 0.70 mol) was changed to $BF_3$ (14.3 g, 0.21 mol; about 0.33 times by mole to 2,6-DMN). The obtained oil layer was analyzed through gas chromatography. As a result, the percent conversion of 2,6-DMN, 2,6-DMNAL yield, and 3,7-DMNAL yield were found to be 33.6%, 5.2%, and 13.5% (2,6-DMNAL/3,7-DMNAL=27.8/72.2).

Thus, when the amount of $BF_3$ was reduced to less than 0.5 times by mole with respect to that of 2,6-DMN, the percent conversion of 2,6-DMN lowered; the 2,6-DMNAL yield considerably lowered, and the 3,7-ratio considerably exceeded 30 mol %.

Example 5

The procedure of Example 1 was repeated, except that starting materials of 2,6-DMN (100.0 g, 0.64 mol), n-heptane (100.0 g), and $BF_3$ (47.8 g, 0.70 mol) were changed to those of 2,6-DMN (50.0 g, 0.32 mol), n-heptane (50.0 g), and $BF_3$ (23.9 g, 0.35 mol; about 1.1 times by mole to 2,6-DMN) (i.e., HF/2,6-DMN=about 50 by mole) and the liquid temperature was maintained at 40° C. for 5 hours instead of at 50° C. for 1 hour. The obtained oil layer was analyzed through gas chromatography. As a result, the percent conversion of 2,6-DMN, 2,6-DMNAL yield, and 3,7-DMNAL yield were found to be 91.6%, 45.2%, and 18.9% (2,6-DMNAL/3,7-DMNAL=70.5/29.5).

Example 6

The procedure of Example 1 was repeated, except that anhydrous HF (320.2 g, 16.0 mol) was changed to anhydrous HF (128.1 g, 6.4 mol; 10 times by mole to 2,6-DMN) and the liquid temperature was maintained at 50° C. for 3 hours instead of at 50° C. for 1 hour. The obtained oil layer was analyzed through gas chromatography. As a result, the percent conversion of 2,6-DMN, 2,6-DMNAL yield, and 3,7-DMNAL yield were found to be 96.3%, 40.8%, and 17.4% (2,6-DMNAL/3,7-DMNAL=70.1/29.9).

Comparative Example 5

The procedure of Example 6 was repeated, except that the liquid temperature was maintained at 10° C. for 5 hours instead of at 50° C. for 3 hours. The obtained oil layer was analyzed through gas chromatography. As a result, the percent conversion of 2,6-DMN, 2,6-DMNAL yield, and 3,7-DMNAL yield were found to be 89.7%, 21.1%, and 60.1% (2,6-DMNAL/3,7-DMNAL=26.0/74.0).

When the reaction was performed at 10° C., which falls within a reaction temperature range generally employed in a known reaction process employing a $HF.BF_3$ catalyst, a high percent conversion of 2,6-DMN was attained but the 2,6-DMNAL yield lowered, and the 3,7-ratio considerably exceeded 30 mol %.

Comparative Example 6

The procedure of Example 6 was repeated, except that the liquid temperature was maintained at −30° C. for 5 hours instead of at 50° C. for 3 hours. The obtained oil layer was analyzed through gas chromatography. As a result, the percent conversion of 2,6-DMN, 2,6-DMNAL yield, and 3,7-DMNAL yield were found to be 21.5%, 13.6%, and 7.3% (2,6-DMNAL/3,7-DMNAL=65.0/35.0).

When the reaction was performed at −30° C., which falls within a reaction temperature range generally employed in a known reaction process employing a $HF.BF_3$ catalyst, the percent conversion of 2,6-DMN lowered, and the 2,6-DMNAL yield considerably lowered.

Comparative Example 7

The procedure of Comparative Example 6 was repeated, except that $BF_3$ (47.8 g, 0.70 mol) was changed to $BF_3$ (295.2 g, 4.35 mol; about 6.8 times by mole to 2,6-DMN). The obtained oil layer was analyzed through gas chromatography. As a result, the percent conversion of 2,6-DMN, 2,6-DMNAL yield, and 3,7-DMNAL yield were found to be 2.5%, 1.1%, and 1.0% (2,6-DMNAL/3,7-DMNAL=54.0/46.0).

Thus, when the reaction was performed at −30° C., which falls within a reaction temperature range generally employed in a known reaction process employing a $HF.BF_3$ catalyst, and the amount of $BF_3$ considerably exceeded 3.5 times by mole with respect to that of 2,6-DMN, the percent conversion of 2,6-DMN considerably lowered, and the 2,6-DMNAL yield considerably lowered.

Example 7

The procedure of Example 1 was repeated, except that $BF_3$ (47.8 g, 0.70 mol) was changed to $BF_3$ (143.4 g, 2.10 mol; about 3.3 times by mole to 2,6-DMN). The obtained oil layer was analyzed through gas chromatography. As a result, the percent conversion of 2,6-DMN, 2,6-DMNAL yield, and 3,7-DMNAL yield were found to be 58.5%, 29.7%, and 10.2% (2,6-DMNAL/3,7-DMNAL=74.4/25.6).

Comparative Example 8

The procedure of Example 1 was repeated, except that $BF_3$ (47.8 g, 0.70 mol) was changed to $BF_3$ (191.2 g, 2.82 mol; about 4.4 times by mole to 2,6-DMN). The obtained oil layer was analyzed through gas chromatography. As a result, the percent conversion of 2,6-DMN, 2,6-DMNAL yield, and 3,7-DMNAL yield were found to be 33.3%, 11.5%, and 4.4% (2,6-DMNAL/3,7-DMNAL=72.3/27.7).

Thus, when the amount of $BF_3$ slightly exceeded 3.5 times by mole with respect to that of 2,6-DMN, the 2,6-DMNAL yield considerably lowered.

INDUSTRIAL APPLICABILITY 2,6-Dimethyl-1-naphthaldehyde produced through the process of the present invention is useful for industrial chemical materials, starting materials for pharmaceuticals, pesticides, optical functional materials, electronic functional materials, etc.

The invention claimed is:

1. A process for producing 2,6-dimethyl-1-naphthaldehyde through formylation of 2,6-dimethylnaphthalene with carbon monoxide, wherein formylation is performed in the presence of hydrogen fluoride in an amount of 5 to 100 times by mole and boron trifluoride in an amount of 0.5 to 3.5 times by mole, with respect to 2,6-dimethylnaphthalene, and at a reaction temperature of 35 to 70° C.

2. The process for producing 2,6-dimethyl-1-naphthaldehyde according to claim 1, wherein the hydrogen fluoride has a water content of 0.1% or less.

3. The process for producing 2,6-dimethyl-1-naphthaldehyde according to claim 1, wherein the formylation is conducted in the presence of heptane as a solvent, and the amount of solvent by mass is from 0.1 to 10 times that of 2,6-dimethylnaphthalene.

* * * * *